(12) United States Patent
Ueno et al.

(10) Patent No.: US 7,682,564 B2
(45) Date of Patent: Mar. 23, 2010

(54) BENZENE DETECTING ELEMENT AND PREPARATION PROCESS OF SAME

(75) Inventors: Yuko Ueno, Tokyo (JP); Akiyuki Tate, Tokyo (JP); Osamu Niwa, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 206 days.

(21) Appl. No.: 10/547,460

(22) PCT Filed: Dec. 17, 2004

(86) PCT No.: PCT/JP2004/018932

§ 371 (c)(1),
(2), (4) Date: Dec. 5, 2005

(87) PCT Pub. No.: WO2005/075954

PCT Pub. Date: Aug. 18, 2005

(65) Prior Publication Data

US 2006/0258015 A1 Nov. 16, 2006

(30) Foreign Application Priority Data

Feb. 6, 2004 (JP) ............................. 2004-030556

(51) Int. Cl.
*G01N 33/00* (2006.01)
(52) U.S. Cl. .................. 422/58; 422/82.01; 436/73; 436/86
(58) Field of Classification Search ........... 423/704, 423/705, 707, 712, 716; 422/55, 82.01; 502/62, 502/64; 436/73, 86

See application file for complete search history.

(56) References Cited

U.S. PATENT DOCUMENTS 5,334,368 A * 8/1994 Beck et al. ................. 423/704

(Continued)

FOREIGN PATENT DOCUMENTS

JP 10-62401 3/1998

(Continued)

OTHER PUBLICATIONS

Experimental and Theoretical Study on Thermodynamic Stabilities of Silyl Cations. Substituent Effect on the Stability of Dimethylphenyllilyl Cation in the Gas Phase. Hirotaka Tashiro, Kiyoshi Kikukaws, Kazutoshi Ikenaga, Nobujiro Shimizu, and Masaaki Mishima Journal of the Chemical Society, Perkin Trans. 2, 1998, 2435-2440.*

(Continued)

*Primary Examiner*—Robert J Hill, Jr.
*Assistant Examiner*—Dwan A Gerido
(74) *Attorney, Agent, or Firm*—Fish & Richardson P.C.

(57) ABSTRACT

The present invention relates to a benzene detecting element capable of detecting benzene selectively and highly sensitively, and a preparation process thereof. The benzene detecting element of the present invention is a mesoporous silicate for detecting benzene selectively and highly sensitively in atmospheric air, and the detecting element has a nanosized fine pore having a highly ordered periodic fine pore structure, and the wall of the nanosized fine pore has a sub-nanosized fine pore. The nanosized fine pore has a pore size of from 0.15 nm to 50 nm in radius, the sub-nanosized fine pore has a pore size of from 0.05 to 0.5 nm in radius, and at least the sub-nanosized fine pore among the fine pores is modified with an organosilicon functional group having a phenyl group, or a silanol group. The present invention also relates to a preparation process of the detecting element.

16 Claims, 6 Drawing Sheets

U.S. PATENT DOCUMENTS

| | | | | |
|---|---|---|---|---|
| 5,364,797 | A | * | 11/1994 | Olson et al. .................. 436/501 |
| 5,902,564 | A | * | 5/1999 | Lujano et al. ................ 423/702 |
| 7,267,812 | B2 | * | 9/2007 | Takahashi et al. ............ 423/712 |

FOREIGN PATENT DOCUMENTS

| | | |
|---|---|---|
| JP | 2000-35810 | 2/2000 |
| JP | 2000-88827 | 3/2000 |
| JP | 2003-021595 | 1/2003 |

OTHER PUBLICATIONS

Stein et al., (2000), "Hybrid Inorganic-Organic Mesoporous Silicates-Nanoscopic Reactors Coming of Age", Adv. Materials 12(19):1403-1419.

Ueno et al., (2004), "High benzene selectivity of uniform sub-nanometre pores of self-ordered mesoporous silicate", Chem. Comm. pp. 746-747.

ISMNT-1, "The first Int'l. Symposium on Micro & Nano Technology", The Waikiki Beach Marriot Resort, Honolulu, Hawaii, Mar. 14-17, 2004.

Ueno et al., (2003), "Improvement of On-Site Microfluidic Benzene, Toluene, Xylene (BTX) Gas Sensor Loaded with Nanostructured Mesoporous Silicate", Sensors, and Materials, 15(8):393-402.

Ueno et al., "Selective Detection of BTX Gas by using Mesoporous Silicate with Uniform Nano-sized Pores", Nanoscience and Nanotechnology on Quantum Particles NNQP 2003, RLNR/Tokyo-Tech 2003 International Symposium, p. 29, Dec. 15-17, 2003.

Ueno et al. (2003), "Portable automatic BTX measurement system with microfluidic dvice using mesoporous silicate adsorbent with nano-sized pores", Sensors and Actuators B 95 pp. 282-286.

Ueno, "Separation and Optical Detection of BTX-Mixture Gases Using a Microfluidic Device", Abst. Of Papers Part 1, $223^{rd,}$, 130. ACS National Meeting 0-8412-3822-7, American Chem. Soc. Orlando, FL Apr. 7-11, 2002.

Ueno et al., (2002) "Microfluidic Device for Detection and Identification of BTX Gases Using a Function of Nano-sized Pores of Mesoporous Silicate" Eurosensors—Book of Abstracts Part 3, pp. 725-726, Sep. 15-18, 2002.

Horiuchi et al., (2002) "Portable System For Selective Detection of Aromatic Voc Mixture—Gases Using a Microfluidic Device", Micro Total Analysis Systems 2002, Proceedings of the μTAS 2002 Symposium, held in Nara, Japan, 1:5360-5380, Nov. 3-7, 2002.

Ueno et al., (2002), "Separate Detection of BTX Mixture Gas by a Microfluidic Device Using A Function of Nanosized Pores of Mesoporous Silica Adsorbent", Analytical Chem. 74(20):5257-5262.

Ueno et al., (2005), "Effect of the calcinations temperature of self-ordered mesoporous silicate on its adsorption characteristics for aromatic hydrocarbons", New J. Chem.29:504-508.

Ueno et al., "High benzene selectivity of mesoporous silicate for BTX gas sensing microfluidic devices", Anal. Bio. Chem. In Press, DOI 10.1007/s00216-004-2974-6.

"Collection by Solid Sorbent and Adsorbent" Shinjikkenkagakukouza 9, "Bunsekikagaku II", Ed. by Shadanhoujin Nipponkagakukai, Maruzen K. K. (In English and Japanese translations).

F2010 "Ultra-sensitive measurement of benzene by a microchip gas sensor" The Japan Society for Analytical Chemistry, May 1, 2004 (In English and Japanese translations).

"Microsensor Using Nano-Porous Material" Journal of The Surface Finishing Society of Japan vol. 53, No. 12, 2002 (In English and Japanese translations).

2Dp03 "Analysis of Sintering-Temperature Dependence of Micropore Size of Mesoporous Silica and Molecular Sieve Phenomenon of Toluene with Respect to Benzene by Using Cylinder Models" (In English and Japanese translations).

NTT Microsystems Integration Laboratories "Mesoporous Silica for Adsorbing Benzene Mounted on a Portable High-sensitive Sensor Application to Detection of Hazardous Organic Gas", Nikkei Advanced Technology Report, Sep. 8, 2003 (In English and Japanese translations).

News Commentary "Successful in Developing a High-performance Portable Benzene gas Sensor" The Journal of The Institute of Electronics, Information and Communication Engineers, vol. 86, No. 7, Jul. 2003 (In English and Japanese translations).

Short Review by Young Researcher "Micro BTX Gas Sensor Using Gas Concentration by Nano-porous Material and Spectroscopic Detection" Researches on Spectroscopy, vol. 52, No. 4 (2003), pp. 225-229 (In English and Japanese translations).

2E07 "Micro BTX Gas Sensor Using Nano-porous Silica Having Uniform Pores" 2003, The Japan Society for Analytical Chemistry, The Japan Society for Analytical Chemistry, May 10, 2003 (In English and Japanese translations).

"Micro BTX Sensor Using Nano-porous Material" (In English and Japanese translations).

50. "Micro BTX Sensor Using Nano-porous Material" Chemical Sensors, vol. 19, Supplement A (2003) (In English and Japanese translations).

3 F7-43 "Influence of an Adsorbent on Separation and Detection of VOC Gas Using Micro Gas Flow Device" (In English and Japanese translations).

3 B4-10 "Benzene Selective Mechanism of Mesoporous Silica Material Applied to BTX Gas Sensor" (In English and Japanese translations).

* cited by examiner

```
┌─────────────────────────────────────────────────────────┐
│    <SYNTHESIS OF DIE FOR NANOSIZED AND SUB-NANOSIZED DIE>│
│       DISSOLVING EO₁₀₀-PO₆₅-EO₁₀₀ (F127) IN DILUTED      │
│            HYDROCHLORIC ACID, STIRRED AT 40°C            │
└─────────────────────────────────────────────────────────┘
                            │
                            ▼
┌─────────────────────────────────────────────────────────┐
│               <SYNTHESIS OF SILICATE FRAME>              │
│   ADDING TEOS TO THE ABOVE SOLUTION, STIRRING, AGING AT 80°C │
│        FOR ONE DAY, THEREAFTER, FILTRATING A PRECIPITATE,│
│      WASHING WITH WATER, AIR-DRYING AT ROOM TEMPERATURE  │
└─────────────────────────────────────────────────────────┘
                            │
                            ▼
┌─────────────────────────────────────────────────────────┐
│                 <REMOVAL OF DIE MOLECULE>                │
│       SINTERING THE ABOVE PRECIPITATE TO OBTAIN SBA-16.  │
│        ROOM TEMPERATURE TO 450°C (8 HOURS), 450°C TO 100°C│
│      (8 HOURS) 100°C TO ROOM TEMPERATURE (NATURAL COOLING)│
└─────────────────────────────────────────────────────────┘
                            │
                            ▼
┌─────────────────────────────────────────────────────────┐
│         <MODIFICATION OF SURFACE BY FUNCTIONAL GROUP>    │
│        REFLUXING SBA-16 AND MEPHETO-SI IN WEIGHT RATIO 1:1│
│                  IN TOLUENE (125°C, 3 HOURS)             │
└─────────────────────────────────────────────────────────┘
                            │
                            ▼
┌─────────────────────────────────────────────────────────┐
│                    <WASHING, DRYING>                     │
│         FILTRATING THE ABOVE PRECIPITATE, WASHING        │
│          (1:1 DICHLOROMETHANE AND DIETHYL ETHER),        │
│                    DRYING (60°C, 3 HOURS)                │
└─────────────────────────────────────────────────────────┘
```

BENZENE DETECTING ELEMENT AND PREPARATION PROCESS OF SAME

TECHNICAL FIELD

The present invention relates to a benzene detecting element for selectively and highly sensitively detecting benzene in atmospheric air, and a preparation process of the same.

BACKGROUND ART

As a benzene detecting element for selectively and highly sensitively detecting benzene slightly present in atmospheric air, there is a detecting element by adsorbing a target molecule with an adsorbent and concentrating (Non-patent Document 1). This adsorbent is one utilizing a substituent which has high affinity with benzene and its analogous aromatic molecule. When using this conventional method, there arise the following problems. Namely, since this conventional method is a separation method where only physicochemical properties are used, it is not suitable to separate benzene from molecules having similar nature or structure to benzene. Moreover, there is expected a method where an element by using a host molecule having sites which identify only benzene molecule is used. However, since production of the element requires a complex synthetic process, the synthesis of the element is difficult as to a stable molecule having a remarkably low reactivity like benzene.

Patent Document 1: JP-A-2003-021595
Non-patent Document 1: SHINJIKKENKAGAKUKOUZA 9, "BUNSEKIKAGAKU II", Ed. by Shadanhoujin NIPPONKAGAKUKAI, MARUZEN K. K.
Non-patent Document 2: A. Stein, B. J. Melde, R. C. Schroden, Adv. Mater. 12(19), 1403 (2000)

DISCLOSURE OF THE INVENTION

The object of the present invention is to provide an element comprising mesoporous silicate for selectively and highly sensitively detecting benzene slightly present in atmospheric air. This detecting element is designed so as to produce a difference in affinity between benzene molecule and an aromatic molecule analogous to benzene. In addition, the object of the present invention is to provide a process for preparing the aforementioned detecting element by employing a relatively easy synthetic method.

In order to solve the aforementioned problems, the benzene detecting element according to the present invention is a benzene detecting element comprising mesoporous silicate for selectively and highly sensitively detecting benzene particularly present in atmospheric air. The detecting element has a nanosized fine pore having a highly ordered periodical fine pore structure, the nanosized fine pore has a sub-nanosized fine pore in its wall surface, the nanosized fine pore has a pore size of from 0.15 nm to 50 nm in radius, the sub-nanosized fine pore has a pore size of from 0.05 nm to 0.5 nm in radius, and at least sub-nanosized fine pore of the fine pores is modified with an organosilicon functional group containing phenyl or silanol. The organosilicon functional group is preferably dimethylphenylsilyloxy ($Me_2PhSiO-$). The nanosized fine pore more preferably has a cubic crystalline structure, and has a pore size of from 1.5 nm to 2.0 nm in radius. The sub-nanosized fine pore exists in the wall of the nanosized fine pore in such a structure as to communicate the nanosized fine pores.

The process of preparation of the benzene detecting element according to the present invention comprises the steps of: heating a solution of $EO_{100}-PO_{65}-EO_{100}$ (EO: ethyleneoxide, PO: propyleneoxide, numerals being the number of molecules in each block) as a die for fine pores; adding thereto a precursor of silicate to form a precipitate; and after drying the precipitate, sintering the precipitate to prepare the benzene detecting element having a nanosized fine pore with a highly ordered periodical fine pore structure and having a sub-nanosized fine pore in the wall surface of the nanosized fine pore. The heating is preferably carried out at a temperature range of from 30° C. to 130° C., and the sintering is preferably carried out at a temperature of from 450° C. to 600° C. According to the process of the present invention, a detecting element having the nanosized fine pore of a pore size of from 0.15 nm to 50 nm in radius and the aforementioned sub-nanosized fine pore of a pore size of from 0.15 to 0.5 nm in radius can be obtained. It is preferable that the process of the present invention further includes a step where a silane coupling agent having phenyl group is reacted with the benzene detecting element to introduce an organosilicon functional group having phenyl group into at least the aforementioned sub-nanosized fine pore. The preferred organosilicon functional group is dimethylphenylsilyl.

According to the present invention, benzene slightly present in atmospheric air can be detected selectively and highly sensitively by controlling, in the mesoporous silicate, the periodic structure of the sub-nanosized fine pore, the pore size of the sub-nanosized fine pore, kind and density of the substituent present on the surface of the inner portion of the sub-nanosized fine pore, and affinity between the inner surface of the sub-nanosized fine pore and benzene molecule. According to the present invention, it was shown that the benzene detecting element capable of detecting selectively and highly sensitively benzene slightly present in atmospheric air and the preparation process thereof can be provided.

BEST MODE FOR CARRYING OUT THE INVENTION

The present invention relates to a benzene detecting element comprising a mesoporous silicate having a three-dimensionally highly ordered periodic fine pore structure and the preparation process thereof. Particularly the detecting element of the present invention has the nanosized fine pore, and the sub-nanosized fine pore in the wall surface of the nanosized fine pore. According to the present invention, the benzene detecting element where the pore size of the sub-nanosized fine pore and the surface properties of the sub-nanosized fine pore are controlled suitably so as to detect benzene selectively is provided. Moreover, according to the present invention, the easy preparation process of the benzene detecting element having such characteristics is provided.

In this application, the "controlling" or "control" means that the physical structure of the surface of the inner portion of the fine pore, and the interaction between the surface of the inner portion of the fine pore and the target molecule (benzene molecule) are selected so as to adsorb the target molecule selectively on the detecting element (namely, the pore size of the inner portion of the fine pore being regulated to the particular range, or suitable substituent being introduced to the surface of the fine pore).

These inventions are explained herein bellow. In the following explanation, the explanation is made by referring to drawings optionally. The inventions described in the drawings are merely an example and does not restrict the present invention.

Firstly, the detecting element of the present invention is explained.

According to the detecting element of the present invention, the mesoporous silicate having the nanosized highly ordered periodic fine pore structure is so controlled that (i) the shape and size of the fine pore, (ii) the structure of the inner surface of the fine pore such as kind and density of the substituent on the surface of the inner portion of the fine pore, and (iii) the affinity with the molecule to be detected (hereinafter also referred to as benzene molecule or target molecule) by variously selecting the substituents on the inner surface of the fine pore, comply with the target molecule. According to the present invention, it is preferable to particularly control the sub-nanosized fine pore. The benzene molecule thereby can be adsorbed on the detecting element selectively.

Figure 1:
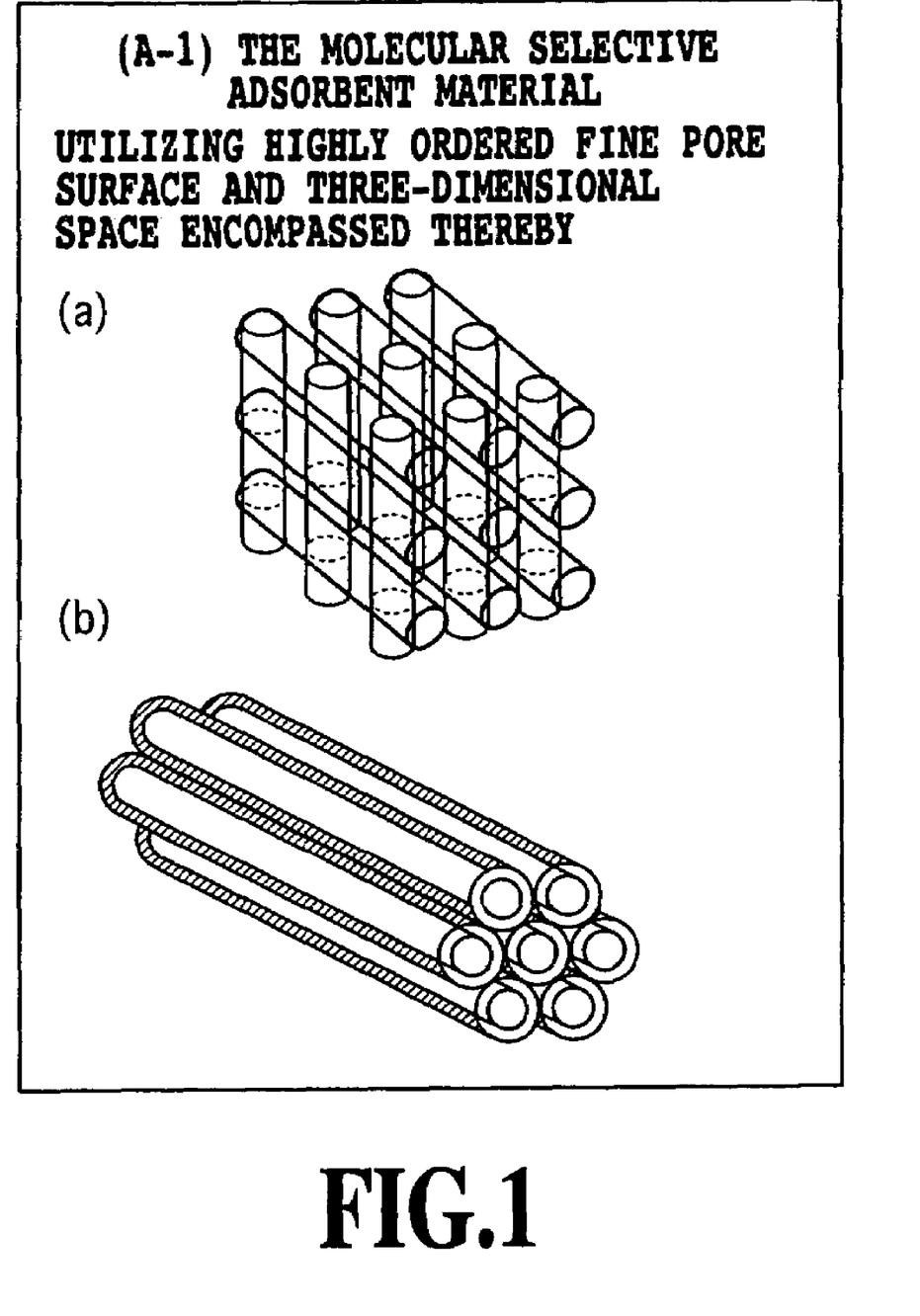
FIG. 1 Figure for explaining the characteristics of the present invention when detecting by utilizing a substituent having high affinity with the target molecule to adsorb the target molecule.

An exemplified detecting element according to the present invention has, for instance as shown in FIG. 1 (A-1) (a) and (b), the three-dimensionally highly ordered periodic fine pore structure for selectively adsorbing the target molecule.

Figure 2:
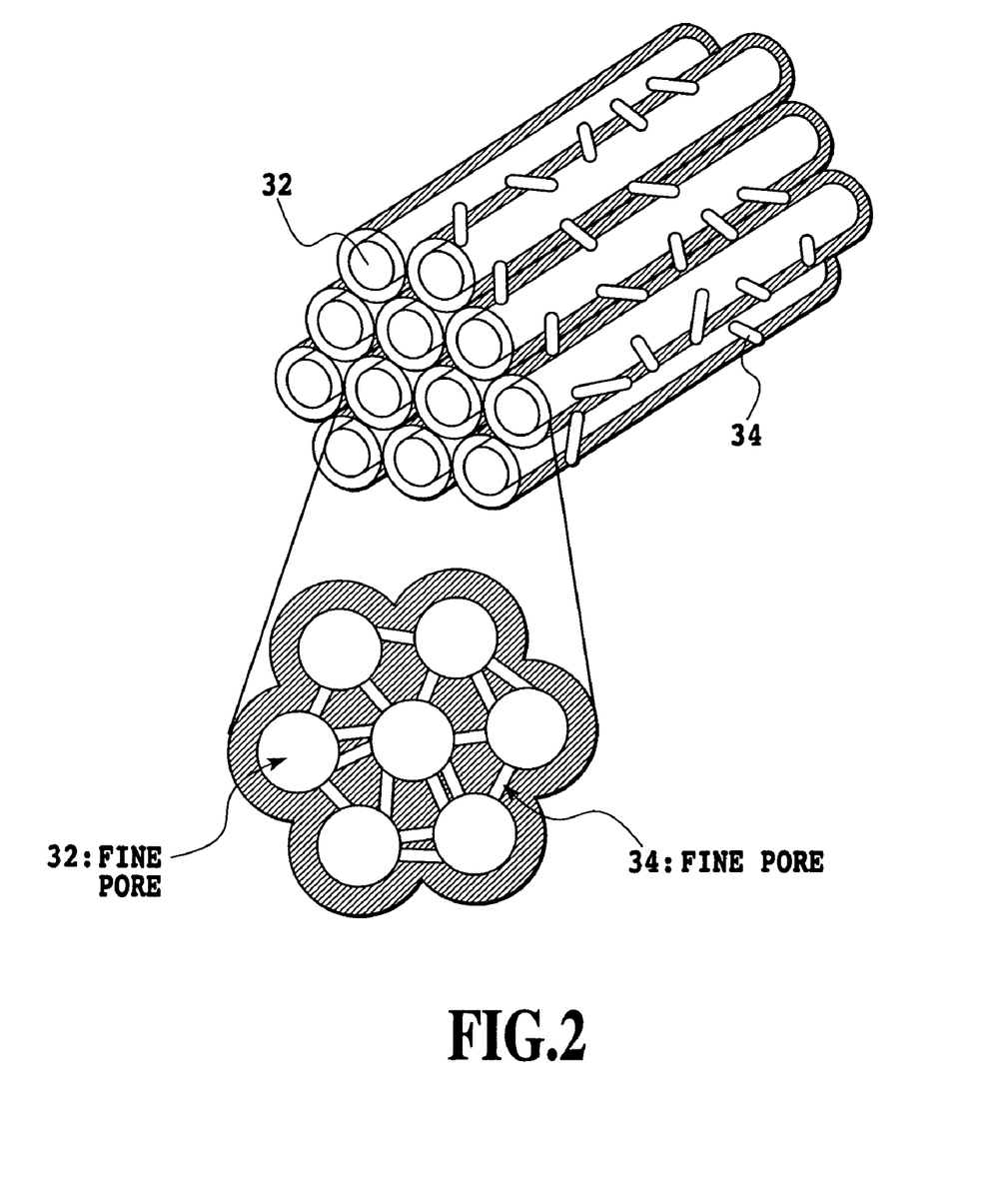
FIG. 2 Figure for showing the characteristics of the detecting element of the present invention.

The detecting element according to the present invention is provided with the highly ordered (for example, fine pore profile such as hexagonal system, cubic system, lamella system) nanosized fine pore (hereinafter also referred to as mesopore), and the sub-nanosized fine pore (hereinafter also referred to as micropore) is formed on the wall surface of this nanosized fine pore. For instance, in case of the detecting element shown in FIG. 2, the mesopore is one so indicated by a fine pore 32, and the micropore is one so indicated by a fine pore 34. The detecting element of the present invention is controlled so that at least the profile of fine pore and the size of fine pore of the sub-nanosized fine pore are suitable to detect benzene, and is made so that the surface of the fine pore is suitable to detect benzene selectively by modifying the surface of the fine pore with various substituents (for example hydroxyl) or an organic functional group (for example organosilicon functional group).

In the present invention, the detecting element is, as mentioned above, the mesoporous silicate, and has a three-dimensionally highly ordered periodic fine pore structure. Preferably the nanosized fine pore has a radius of not less than 0.5 nm and not more than 50 nm, and the sub-nanosized fine pore present in the wall surface of the nanosized fine pore preferably has a radius of not less than 0.05 nm and not more than 0.5 nm. And, it is preferred that at least the surface of this sub-nanosized fine pore is modified by a substituent having affinity with benzene (for example silanol group) or an organic functional group (for example organosilicon functional group).

In the present invention, the detecting element has preferably a periodic cubic structure, and this has the nanosized fine pores which are aligned in high order. On the wall surface thereof, there preferably exists the sub-nanosized fine pore so as to communicate the nanosized fine pores. Further, the nanosized fine pore has a pore size of from 1.5 nm to 2.5 nm in radius, and the aforementioned sub-nanosized fine pore has a pore size of larger than a half size of the benzene molecule (about 0.3 nm) in radius, preferably in the range of from 0.2 to 0.5 nm in radius (that is, 0.15 nm to 0.5 nm, or preferably 0.2 nm to 0.5 nm). In addition, a fine pore size distribution of the sub-nanosized fine pore has a half value width in the center portion of not more than 0.06 nm, preferably 0.05 nm±0.01 nm. Namely, the benzene detecting element has a size for accommodating only one molecule of benzene or larger, but a size of being difficult to adsorb other molecules (for example toluene). The half value width is, as mentioned above, not more than 0.06 nm, and when the distribution becomes larger, molecules other than benzene may enter therein. By using these fine pore structural mesoporous silicates, benzene can be selectively adsorbed and benzene can be detected at a high sensitivity.

In the detecting element of the present invention, the nanosized fine pore has a periodic structure. The structure of the sub-nanosized fine pore may not be periodical. Accordingly, the word "periodic structure" or "three-dimensional periodic structure" means a structure with respect to the nanosized fine pore. In addition, the nanosized fine pore and the sub-nanosized fine pore are both uniform in pore size.

According to the present invention, the surface of the fine pore, particularly the surface of the sub-nanosized fine pore preferably contains silanol as the substituent. Further the surface of the sub-nanosized fine pore is preferably modified with the organic functional group having phenyl group. Particularly according to the present invention, the aforementioned organic functional group is preferably dimethylphenylsilyl, methylphenylsilyl or diphenylsilyl, most preferably dimethylphenylsilyl.

In the present invention, the organic functional group preferably bonds to the surface of the fine pore of the mesoporous silicate via one Si—O— bond as shown in the following Table 1.

TABLE 1

| Substituent on Si | (A) Me₂Ph | (B) Ph₂H | (C) MePh |
|---|---|---|---|
| Bonding structure to silicate surface | Ph-Si(CH₃)(CH₃)-O-silicate | Ph-Si(H)(Ph)-O-silicate | H₃C-Si(Ph)(-O-)(-O-)-silicate |
| Bonding form | One SiO bond | One SiO bond | Two SiO bonds |
| Characteristics | Easy interaction because of easy moving | There are two interactable structures | Hard to interact because it's difficult to move |

As shown in Table 1, when the forms of bond are shown as (A) and (B), it seems that the organic functional group moves relatively freely on the mesoporous silicate and the molecule to be detected (benzene molecule) can be easy to have interaction with the phenyl group on the organic functional group. On the other hand, when the organic functional group is bonded through two Si—O groups on the mesoporous silicate as shown in (C), there is a case where the organic functional group cannot move freely, and the interaction between the molecule to be detected (benzene molecule) and the organic functional group is suppressed.

Also according to the present invention, even when the forms of bond are shown as (A) and (B), there is a case where difference in the selectivity may be caused. For example, when modifying with the organic functional group having the substituent shown as the above (B), it is possible to detect the benzene molecule selectively. However, in case of the combination with the mesoporous silicate represented by SBA-16 mentioned hereinafter, there is a case where, in the detection of a gas mixture of benzene and toluene, difference in the selectivity between benzene and toluene may be occurred between the case where modifying with the functional group having the substituent (A) and the case where modifying with the functional group having the substituent (B) (see EXAMPLE).

The reason why the above difference in selectivity is caused seems that since there are two benzene molecules in the organic functional group such as the group (B), the selectivity thereof is lowered due to its steric hindrance, but the reason is not tied up by this theory. Therefore according to the present invention, the most preferable benzene detecting element is the mesoporous silicate modified with an organic functional group and is SBA-16 where the surface of the fine pore thereof is modified with dimethylphenylsilyl group. Highly selective detection of benzene can be achieved by this combination.

As is explained, according to the present invention, by modifying with the aforementioned functional group, the steric structure of the inner portion of the fine pore can be made into a structure that adsorbs benzene easily, and affinity to benzene can be enhanced higher. According to the benzene detecting element of the present invention, the benzene-adsorbing ability and benzene-concentrating ability in the sub-nanosized fine pore are enhanced to increase the benzene-selective detection ability, whereby a highly sensitive detection can be achieved.

According to the present invention, the selective concentration of a molecule which is difficult to be adsorbed selectively only by three-dimensional structure or surface affinity can be realized by using, in the synthesis of the mesoporous silicate, temperature of synthesis, degree of acidity, substance of die for the fine pore (surface active agent or self-organizing polymer), sintering temperature and physical stimulations such as light or heat to control the shape and size of the fine pore, the kind and density of the substituent or organic functional group on the surface of the inner portion of the fine pore and the like, and affinity between the inner surface of the fine pore and the target molecule.

Moreover, according to the present invention, the selective separation and concentration of the benzene molecule can be realized by controlling the inner portion of the fine pore of the mesoporous silicate having the aforementioned highly ordered periodic fine pore structure suitable to adsorb the benzene molecule. A control of the inner portion of the fine pore of the mesoporous silicate is achieved, after synthesis, by introducing the organic functional group into the inner portion of the nanosized fine pore, or by controlling the kind (for example silanol group) and density of the substituent on the inner surface of the fine pore with chemicals such as an acid or an alkali or through physical oxidation-reduction reaction.

In addition, according to the mesoporous silicate having the fine pore structure used in the present invention, when bonding an organic functional group having a substituent of a high affinity to benzene (for example organosilicon functional group) to the mesoporous silicate, the benzene molecule interacts not only with such a functional group in one direction like two-dimensional surface, but also, for instance, with the upper and lower functional groups in the pore, whereby three-dimensional interaction is produced. Such an action seems to be a factor to separate the benzene molecule highly selectively.

Next, the preparation process of the benzene detecting element is explained.

The present invention provides a preparation process of the benzene detecting element. According to the preparation process of the benzene detecting element, a solution containing a substance for a die of the fine pore is heated to a temperature of from 30 to 130° C., a silicate precursor is added thereto to produce a precipitate, and, after drying the precipitate, the precipitate is sintered at a given temperature. Thereby, the mesoporous silicate of the benzene detecting element of the present invention can be obtained. The substance of the die for the nanosized fine pore is preferably $EO_{100}$—$PO_{65}$-$EO_{100}$ (EO: ethyleneoxide, PO: propyleneoxide, numerals being the number of molecules in each block) (hereinafter also referred to as F127).

According to the preparation process of the present invention, though there may be used other than the aforementioned F127, for example EO20-PO70-EO20 and the like, as the substance for die, it is preferable to use F127. The reason is that difference in selectivity may be caused among the mesoporous silicates obtained from those dies. The reason why such difference in selectivity is caused seems that when using EO20-PO70-EO20 as the substance for die, the obtained mesoporous silicate (hexagonal system) has a smaller surface area of the nanosized fine pore than that of mesoporous silicate (cubic system) obtained by using F127, and as a result, the number of exposed sub-nanosized fine pores is reduced in the mesoporous silicate obtained by using EO20-PO70-EO20.

A solution (for example diluted hydrochloric acid) containing the aforementioned substance (F127) for die is heated to a temperature of from 30° C. to 130° C., and to the solution added a silicate precursor (for example TEOS (tetraethylorthosilicate) may be used) to form a precipitate. After drying the precipitate, the dried precipitate is sintered at a temperature of from 450° C. to 600° C. to prepare the benzene detecting element of the present invention. The mesoporous silicate obtained from the above materials and through the procedures is referred as SBA-16 in the specification.

When the reaction temperature (temperature of the solution) is out of the range of from 30 to 130° C., there is the possibility that good fine pore cannot be obtained. Also, when the sintering temperature is higher than 600° C., crystallization is advanced, and there is the possibility that the fine pore may become small. When the fine pore becomes small, the density of the silanol group on the surface of the fine pore becomes lowered, and thus the selective adsorption may not be caused. When lower than 450° C., there is the possibility that removal of the substance for die of fine pore such as a block copolymer is not sufficient.

According to the present invention, a detecting element may be formed by, after adding the silicate precursor to the solution for die, applying onto a substrate (for example waveguide type chip) to form a thin film, and then removing the substance for die.

The benzene detecting element obtained according to the process of the present invention has, as mentioned above, the three-dimensionally highly ordered periodic nanosized fine pore structure, and the sub-nanosized fine pores exist on the wall thereof.

The silanol group exists on the prepared mesoporous silicate as mentioned above. The silanol group may be increased by, for example, treating with a sulfuric acid-hydrogen peroxide solution. Also, the silanol group may be decreased by heating the mesoporous silicate or surface-treating with a neutral to acidic solution whereby hydrophilic property can be lowered. The acidic solution to be used, includes for example, hydrochloric acid, nitric acid, sulfuric acid and the like. These solutions preferably have, for example, a pH of from 1 to 6. Moreover, according to the present invention, by treating the surface with such a solution as a mixed solution of sulfuric acid and hydrogen peroxide (mixed ratio; for example, conc. sulfuric acid (96%): hydrogen peroxide: water=2:1:1 to 3:1:1), the surface of the fine pore can be made hydrophilic. Namely, it is possible to control an amount of silanol on the surface of the fine pore.

In the preparation process of the present invention, it is preferred to modify the surface of the fine pore with the functional group, preferably by applying a coupling agent to the aforementioned mesoporous silicate. The functional group is an organic functional group, and preferably dimethylphenylsilyl, methylphenylsilyl or diphenylsilyl, most preferably dimethylphenysilyl. The silane coupling agent reacts with the silanol group on the surface of the fine pore of the mesoporous silicate to bond the organosilicon functional group to the surface of the fine pore.

In the present invention, it is most preferable that the detecting element is prepared by using the particular mesoporous silicate precursor, and modifying the surface of the fine pore of the obtained detecting element with the particular organic functional group like dimethylphenylsilyl. This is because the benzene molecule can be selectively detected due to the fact that the detecting element of the present invention has the particular crystalline structure and the inner portion of the fine pore is modified with the particular organic functional group.

As mentioned above, the benzene detecting element is a detecting element capable of separating selectively and concentrating the benzene molecule, by suitably selecting the pore size, and/or kind and size and/or density of the functional group to be introduced into the pore to utilize both of effect of physical size of the fine pore and steric effect of the surface of the inner portion of the fine pore (size effect), and effect of chemical affinity simultaneously and three-dimensionally. Further, the detecting element can be prepared without a complex synthesis method, and can achieve a high selectivity.

According to the present invention, selective detection of benzene can be carried out by using the aforementioned detecting element. The detecting method can be achieved by, for instance, a device provided with at least a separation part for selectively separating the benzene molecule and a detection part for detecting the target substance separated in the separation part, including the detecting element of the present invention. Example of such a device is, for instance, one disclosed in JP-A-2003-021595 (Patent Document 1). In the present invention, the detection part can be assembled into the separation part.

For the detection of the benzene molecule, there may be employed a method where the benzene molecule selectively adsorbed on the detecting element is released, for example, with heating, and the released concentrated gas is measured optically, or a method where optical measurement is carried out in the state in which the benzene molecule is adsorbed and concentrated on the detecting element. The optical measurement is not particularly limited, and, for example, may be carried out by using an ultraviolet detector. Accordingly, the target molecule can be detected.

EXAMPLES

In the following, the present invention is more specifically explained by referring to Examples. The present invention is, however, not limited to only the following examples.

Example 1

Figure 3:
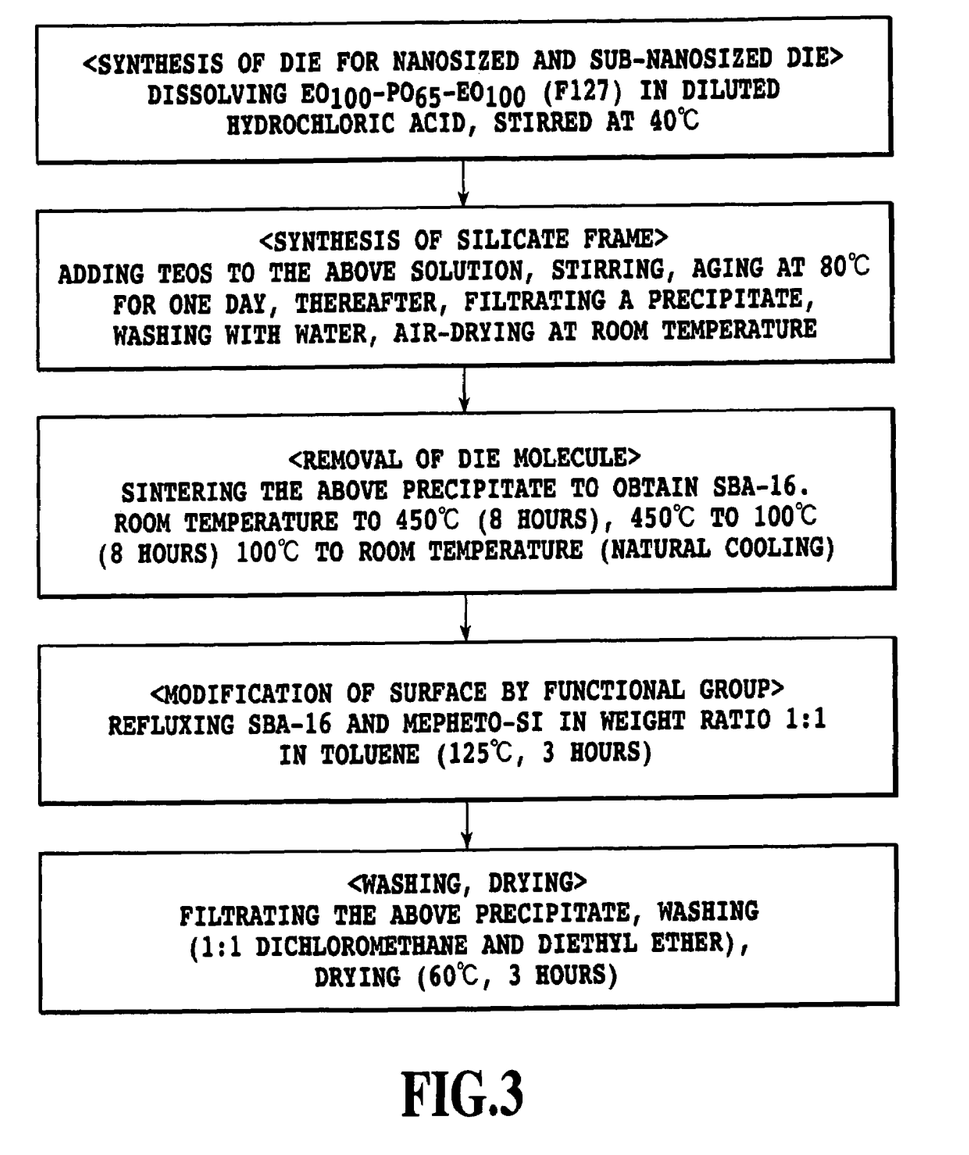
FIG. 3 Figure for showing the flow of the preparation process of the material of the present invention.

The detecting element of the present invention was prepared as mentioned below. The preparation flow is shown in FIG. 3.

The block copolymer EO$_{100}$-PO$_{65}$-EO$_{100}$ (EO: ethyleneoxide, PO: propyleneoxide) (F127) is dissolved in a diluted hydrochloric acid. The obtained solution is stirred at a dissolving temperature Ts=40° C., and then TEOS (tetraethylorthosilicate) as a silicate precursor is added to produce a precipitate. The solution and precipitate are aged at 80° C. for one day, and thereafter filtrated, washed with water, and air-dried at room temperature. Finally, gentle sintering is carried out. The sintering is conducted by, after heating up from room temperature to 450° C. in 8 hours, allowed to stay at 450° C. for 6 hours, cooling from 450° C. to 100° C. in 8 hours, and finally returning to room temperature by natural cooling.

According to the above process, a mesoporous silicate (SBA-16) having uniform fine pores of two kinds, i.e. a nano-sized fine pore having a diameter of 4.0 nm and a sub-nano-sized fine pore having a diameter of 0.44 nm was prepared. In this case, the nanosized fine pore has a cubic system periodic structure, and the sub-nanosized fine pore is present on the wall of the nanosized fine pore so as to communicate the nanosized fine pores. There was 40% to 60% of silanol group on the surface of the thus prepared fine pore of the mesoporous silicate. The silanol group can be increased by treating with a sulfuric acid-hydrogen peroxide solution (a mixed solution of sulfuric acid and hydrogen peroxide solution (ratio; conc. sulfuric acid (96%): hydrogen peroxide: water=2: 1:1 to 3:1:1)).

The surface of the mesoporous silicate can be modified with any organic functional group by selecting a coupling agent, and a density thereof can be controlled by the aforementioned surface treatment. Some examples are reported (Non-patent Document 2). In this EXAMPLE, Me$_2$PhEtO—Si (dimethylphenylethoxysilane) was used as a coupling agent. The functional modification process was carried out by using TEFLON (registered trademark) in an argon gas. SBA-16 and Me$_2$PhEtO—Si are mixed in toluene at a weight ratio of 1:1, and refluxed at 125° C. for 3 hours. After cooling to room temperature, the precipitate is filtrated, and washed with a 1:1 mixed solution of dichloromethane and diethyl ether. A benzene detecting element was obtained by drying at 60° C. for 3 hours.

This is assembled to, for example, a micro flow cell (for instance, one disclosed in JP-A-2003-021595), and a quantitative and selective detection of benzene from each of mixed gases of benzene, toluene, o-xylene in a low concentration of from ppb to ppm level is carried out.

Figure 4:
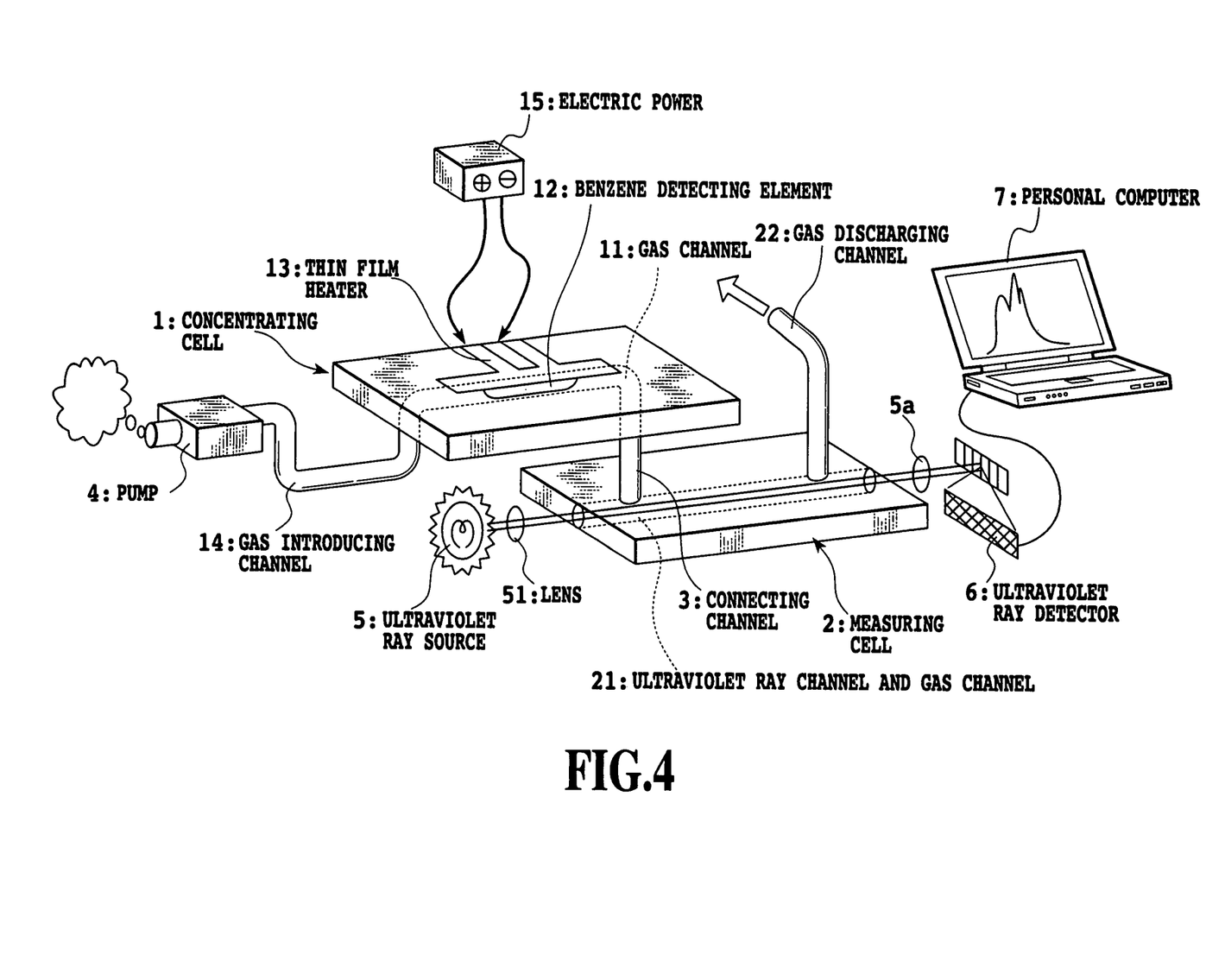
FIG. 4 Figure for explaining the apparatus used in the present invention in EXAMPLE 1

The flow channel of the micro flow cell shown in FIG. 4 was charged with the mixed gases containing benzene, toluene, and o-xylene.

The micro flow cell is provided with a concentrating cell 1 and a measuring cell 2. The concentrating cell 1 is provided with a gas channel 11 for flowing a gas to be measured, a benzene detecting element 12 incorporated within the gas channel 11 and a thin film heater 13 for heating a substance adsorbed and immobilized on the benzene detecting element 12. On the other hand, the measuring cell 2 is provided with an ultraviolet ray channel and gas channel 21 for flowing the gas of a substance to be measured from the gas channel 11, and passing through an ultraviolet ray for measuring. In addition, the measuring cell is provided with a connecting channel 3 for connecting and communicating the gas channel 11 and the ultraviolet ray channel and gas channel 21, and a gas introducing channel 14 for introducing the gas to be measured into the gas channel 11 of the concentrating cell 1, and a gas discharging channel 22 for discharging the gas which has been measured. Numeral 4 is a pump for introducing a gas into the gas introducing channel 14, 15 is an electric power for heating the thin film heater 13, 5 is a light source for an incident ultraviolet ray into the ultraviolet ray channel and gas channel 21, 5a is a lens for focusing the ultraviolet ray, 6 is an ultraviolet ray detector for detecting the ultraviolet ray emitted from the ultraviolet ray channel and gas channel 21, 7 is a personal computer.

In the following, an example of procedures for measurement is explained. An air containing benzene is introduced into the gas channel 11 from the gas introducing channel 14 of the concentrating cell 1 by the pump 4, and the benzene gas is adsorbed and immobilized on the benzene detecting element 12 incorporated within the gas channel 11. After passing the air for a given period of time, the thin film heater 13 is turned on by the electric power 15 to heat, and a temperature of the benzene gas adsorbed on the benzene detecting element 12 is elevated to a heat-desorbed temperature to desorb benzene. This desorbed and separated gas is introduced through the connecting channel 3 into the ultraviolet ray channel and gas channel 21 of the measuring cell 2. By using an optical fiber connected to the ultraviolet ray source 5 and the ultraviolet ray detector 6, detection of a contaminating substance is carried out by absorption spectrophotometry. After measurement, the gas is discharged from the gas discharging channel 22. The data are processed by the personal computer 7.

Figure 5A:
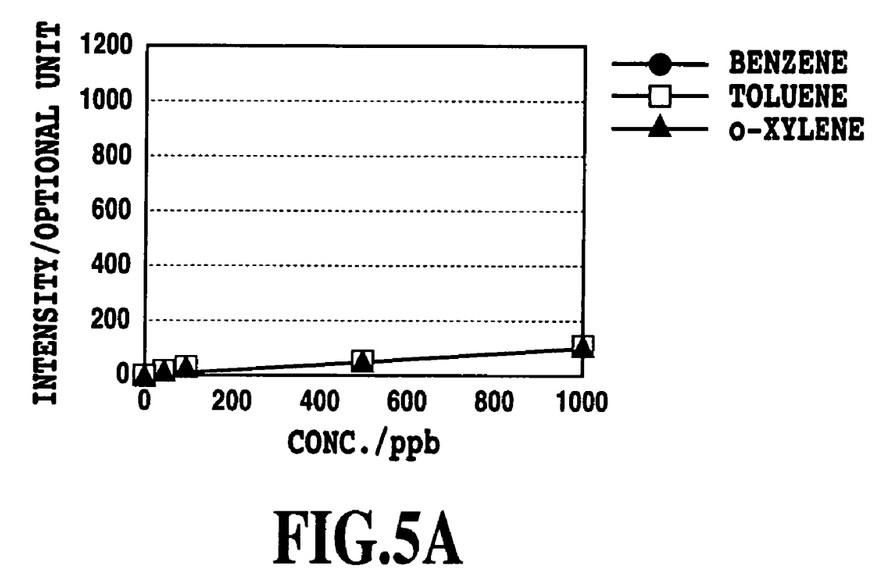
FIG. 5A Figure for comparing the signal intensities of benzene, toluene and o-xylene obtained in EXAMPLE 1 by carrying out the detection of the benzene gas according to the conventional method by using the apparatus shown in FIG. 4.
Figure 5B:
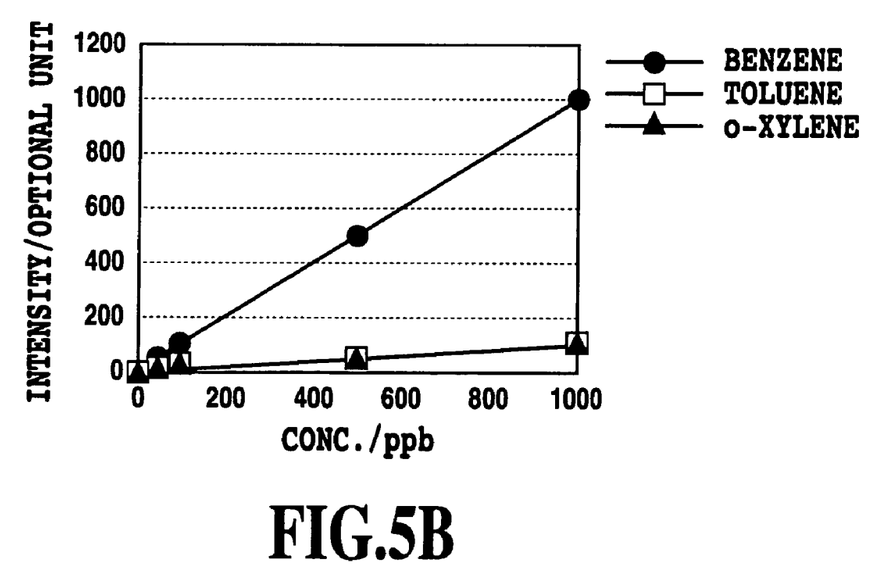
FIG. 5B Figure for comparing the signal intensities of benzene, toluene and o-xylene obtained in EXAMPLE 1 by carrying out the detection of the benzene gas according to the present invention by using the apparatus shown in FIG. 4.

Toluene and o-xylene are molecules which are very analogous to benzene in structure, configuration and nature, and it is difficult to adsorb benzene selectively by using a conventional material. However, when using the present invention, it has been found that a ratio of detecting signal intensity of benzene: toluene: o-xylene is about 10:1:1, and a detecting sensitivity as to benzene becomes high (FIGS. 5A-5B). FIG. 5A shows a graph representing a signal intensity of a conventional benzene detecting element, FIG. 5B shows a graph representing a signal intensity of the benzene detecting element of the present invention. Specifically, as shown in FIG. 5A, benzene, toluene and o-xylene had the same signal intensity over the concentration range of from 0 to 1000 ppb (in the figure, the black circles for benzene are overlapped with the symbols of toluene (white square) and o-xylene (black triangle). In the concentration range of from 0 to 1000 ppb, as shown in FIG. 5B, though toluene and o-xylene had the same signal intensity, benzene shows a signal intensity 10 times stronger than those of toluene and o-xylene over this concentration range.

As is clear from the results, according to the present invention, benzene slightly present in atmospheric air can be detected selectively at a high sensitivity.

Example 2

Figure 6A:
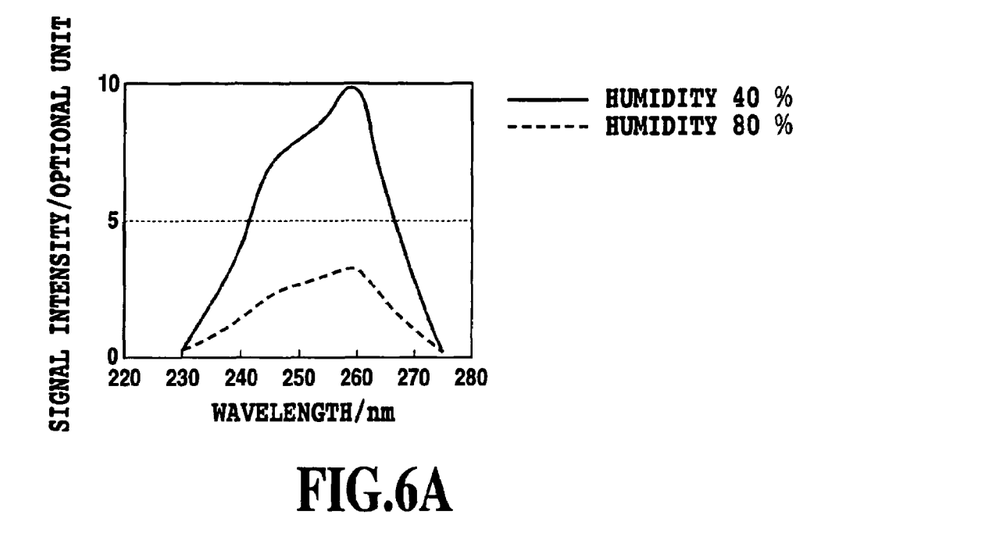
FIG. 6A Figure for showing the signal intensity of benzene according to the conventional method in EXAMPLE 2.
Figure 6B:
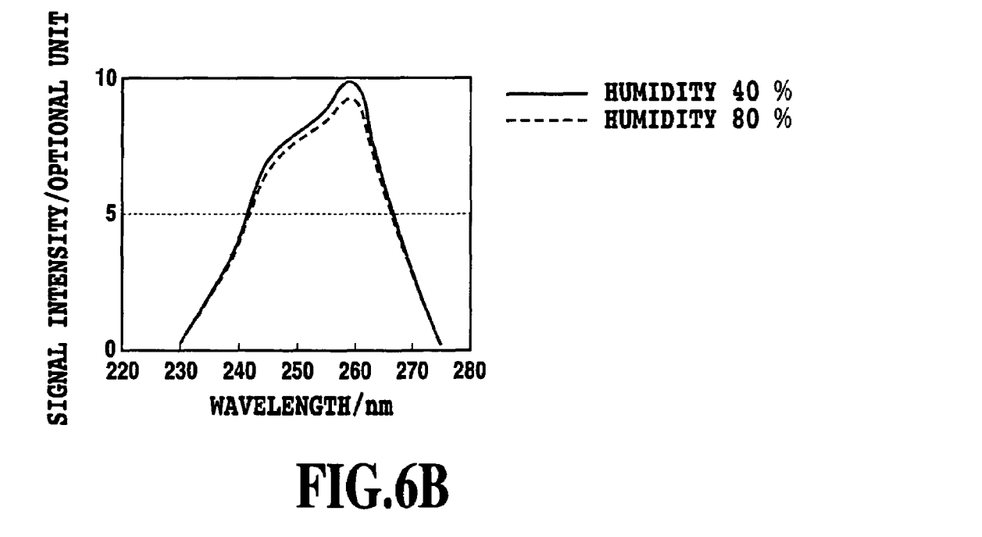
FIG. 6B Figure for showing the signal intensity of benzene according to the present invention in EXAMPLE 2.

Detection of an exhaust gas from an automobile was carried out by the same manner as in EXAMPLE 1. There are cases where a humidity of the exhaust gas is 80% or higher, and as to the number of molecules contained in the gas, water is predominantly large, therefore, interference by water causes serious problems in a detecting method by using a conventional adsorbent. However, when using the present invention, regardless of humidity, a very strong signal of benzene was detected (FIGS. 6A-6B). FIG. 6A shows a graph representing a signal intensity of a conventional benzene detecting element, and FIG. 6B shows a graph representing a signal intensity of the benzene detecting element of the present invention. From the above, according to the present invention, benzene slightly present in atmospheric air can be detected selectively at a high sensitivity.

Comparative Examples 1, 2

In the comparative experiments, the variation of selectivity of benzene was studied with combinations of SBA-16 and organic functional groups for modifying SBA-16.

Mesoporous silicate modified with a functional group was prepared in the same procedures as in EXAMPLE 1, except that the substituent (B) or (C) on Si shown in the following Table 2 was introduced. By using the mesoporous silicate (modified with dimethylphenysilyl) prepared in EXAMPLE 1 and the obtained mesoporous silicates modified with the functional groups, the benzene molecule in benzene-toluene (100 ppb mixed gas) was detected according to the same procedures described in EXAMPLE 1. The results of the detection were shown in Table 2 together. The results of the detection (results of the experiments) are shown as a relative ratio where the selectivity of the mesoporous silicate modified with the functional group having the substituent (C) is assumed to be 1.

INDUSTRIAL APPLICABILITY

The present invention can be utilized in the analytical fields where a specified molecule is selectively detected. Particularly, the present invention uses the benzene detecting element comprising the mesoporous silicate whose fine pore is either not modified or modified with a particular substituent. This detecting element is one controlling the structure of the sub-nanosized fine pore, pore size, state of modification on the surface of the inner portion of the fine pore (kind, density and the like of the organic functional group having a particular substituent), and affinity between the inner surface of the fine pore and benzene molecule. By using the detecting element of the present invention, benzene, slightly present in atmospheric air can be detected selectively and highly sensitively.

The invention claimed is:

1. A benzene detecting element comprising a mesoporous silicate for selectively and highly sensitively detecting benzene, said detecting element comprising: a first nanosized fine pore having a highly ordered periodical fine pore structure,

TABLE 2

| Substituent on Si | (A) Me$_2$Ph | (B) Ph$_2$H | (C) MePh |
|---|---|---|---|
| Bonding structure to silicate surface |  |  |  |
| Bonding form | One SiO bond | One SiO bond | Two SiO bonds |
| Characteristics | Easy interaction because of easy moving | There are two interactable structures | Hard to interact because it's difficult to move |
| Effects | Exhibit high selectivity | Hard to interact because of bulky steric hindrance | No selectivity |
| Experimental results | >5 | about 1 | 1 |

As is clear from the above results, though the benzene molecule can be detected in the case of modifying with the organic functional groups having substituent (B) or (C) on Si of the above Table, the selectivity of the mesoporous silicate modified with the functional group having the substituent (A) on Si is superior. Particularly the selectivity of the mesoporous silicate modified the functional group having the substituent (B) on Si was lowered in the combination with SBA-16. It seems that in this combination, since the organic functional group contains two benzene molecules on Si, the selectivity was lowered due to steric hindrance.

Besides, the separation between benzene and toluene is more difficult than the separation between benzene and xylene. Accordingly, the most preferable benzene detecting element of the present invention has excellent selectivity.

wherein the first nanosized fine pore has a sub-nanosized fine pore in its wall surface, the sub-nanosized fine pore is a conduit connecting the first nanosized fine pore with a second nanosized fine pore so that the first and second nanosized fine pores communicate with each other, the first nanosized fine pore has a pore size of from 0.15 nm to 50 nm in radius, the sub-nanosized fine pore has a pore size of from 0.05 nm to 0.5 nm in radius, at least the sub-nanosized fine pore of the fine pores comprises an organosilicon functional group containing a phenyl group, or a silanol group, and the organosilicon functional group or the silanol group interacts intermolecularly with a target benzene molecule.

2. The benzene detecting element of claim 1, wherein the first nanosized fine pore has a cubic crystalline structure, and has a pore size of from 1.5 nm to 2.0 nm in radius.

3. The benzene detecting element of claim 1, wherein a fine pore size distribution of the sub-nanosized fine pore has a half value width in the center portion of 0.05 nm±0.01 nm.

4. The benzene detecting element of claim 1, wherein the organosilicon functional group is a dimethylphenylsilyl ($Me_2PhSi-$) group.

5. The benzene detecting element of claim 4, wherein the dimethylphenylsilyl group interacts with a target benzene molecule by an intermolecular affinity between the phenyl group on the dimethylphenylsilyl group and the benzene molecule, thereby achieving a high selectivity of benzene.

6. A preparation process of a benzene detecting element of claim 1 comprising the steps of: heating a solution of EO100-PO65-EO100 (EO: ethyleneoxide, PO: propyleneoxide, numerals being the number of molecules in each block) as a die for fine pores; adding thereto a precursor of silicate to form a precipitate; and after drying the precipitate, sintering the precipitate to prepare the benzene detecting element.

7. The preparation process of a benzene detecting element of claim 6, wherein the heating is carried out at a temperature range of from 30° C. to 130° C.

8. The preparation process of a benzene detecting element of claim 6, wherein the sintering is carried out at a temperature of from 450° C. to 600° C.

9. The preparation process of a benzene detecting element of claim 6, wherein the nanosized fine pore has a pore size of from 0.15 nm to 50 nm in radius and the sub-nanosized fine pore has a pore size of from 0.05 to 0.5 nm in radius.

10. The preparation process of a benzene detecting element of claim 6, further comprising a step where a silane coupling agent having a phenyl group is reacted with the benzene detecting element to introduce an organosilicon functional group having a phenyl group into at least the sub-nanosized fine pore.

11. The preparation process of a benzene detecting element of claim 10, wherein the organosilicon functional group is a dimethylphenylsilyl group.

12. A benzene detecting element, comprising:
a mesoporous silicate comprising first and second nanosized fine pores, the first nanosized fine pore having a sub-nanosized fine pore in its wall surface;
wherein the sub-nanosized fine pore is a conduit connecting the first nanosized fine pore with the second nanosized fine pore so that the first and second nanosized fine pores communicate with each other, the first nanosized fine pore has a pore size of from 0.15 nm to 50 nm in radius, the sub-nanosized fine pore has a pore size of from 0.05 nm to 0.5 nm in radius, and at least the sub-nanosized fine pore of the fine pores is covalently attached to an organosilicon functional group containing a phenyl group through a Si—O bond.

13. The benzene detecting element of claim 12, wherein the first nanosized fine pore has a cubic crystalline structure, and has a pore size of from 1.5 nm to 2.0 nm in radius.

14. The benzene detecting element of claim 12, wherein a fine pore size distribution of the sub-nanosized fine pore has a half value width in the center portion of 0.05 nm±0.01 nm.

15. The benzene detecting element of claim 12, wherein the organosilicon functional group is a dimethylphenylsilyl ($Me_2PhSi-$) group.

16. The benzene detecting element of claim 15, wherein the dimethylphenylsilyl group interacts with a target benzene molecule by an intermolecular affinity between the phenyl group on the dimethylphenylsilyl group and the benzene molecule, thereby achieving a high selectivity of benzene.

* * * * *

UNITED STATES PATENT AND TRADEMARK OFFICE
CERTIFICATE OF CORRECTION

PATENT NO.        : 7,682,564 B2
APPLICATION NO.   : 10/547460
DATED             : March 23, 2010
INVENTOR(S)       : Yuko Ueno, Akiyuki Tate and Osamu Niwa

It is certified that error appears in the above-identified patent and that said Letters Patent is hereby corrected as shown below:

Title Page, Column 2 (Other Publications)

Line 3, delete "Dimethylphenyllilyl" and insert -- Dimethylphenylsilyl --.

Signed and Sealed this

Eighth Day of June, 2010

David J. Kappos
*Director of the United States Patent and Trademark Office*